(12) United States Patent
Curley

(10) Patent No.: US 10,022,176 B2
(45) Date of Patent: *Jul. 17, 2018

(54) LOW PROFILE FLUID ENHANCED ABLATION THERAPY DEVICES AND METHODS

(75) Inventor: Michael G. Curley, Weston, MA (US)

(73) Assignee: Thermedical, Inc., Waltham, MA (US)

(*) Notice: Subject to any disclaimer, the term of this patent is extended or adjusted under 35 U.S.C. 154(b) by 459 days.

This patent is subject to a terminal disclaimer.

(21) Appl. No.: 13/586,559

(22) Filed: Aug. 15, 2012

(65) Prior Publication Data

US 2014/0052117 A1 Feb. 20, 2014

(51) Int. Cl.
*A61B 18/04* (2006.01)
*A61B 18/00* (2006.01)
*A61B 90/00* (2016.01)

(52) U.S. Cl.
CPC .............. *A61B 18/04* (2013.01); *A61B 90/37* (2016.02); *A61B 2018/00577* (2013.01); *A61B 2018/00815* (2013.01); *A61B 2018/00821* (2013.01); *A61B 2018/046* (2013.01)

(58) Field of Classification Search
CPC .............. A61B 2218/002; A61B 18/04; A61B 18/1492; A61B 17/32; A61B 17/32002; A61B 18/12; A61B 18/1206; A61B 18/14; A61B 18/1442; A61B 18/1445;
(Continued)

(56) References Cited

U.S. PATENT DOCUMENTS

| 4,160,455 A | 7/1979 | Law |
| 4,424,190 A | 1/1984 | Mather, III et al. |
| 5,190,538 A | 3/1993 | Hussein et al. |

(Continued)

FOREIGN PATENT DOCUMENTS

| CN | 1341462 A | * | 3/2002 |
| CN | 1119127 C | | 8/2003 |

(Continued)

OTHER PUBLICATIONS

International Search Report and Written Opinion for Application No. PCT/US2013/053977, issued Nov. 14, 2012. (20 pages).

(Continued)

*Primary Examiner* — Rex R Holmes
(74) *Attorney, Agent, or Firm* — Nutter McClennen & Fish LLP

(57) ABSTRACT

Low profile devices and methods for delivering fluid enhanced ablation therapy are provided herein. In one embodiment, an ablation device is provided that includes an elongate body having proximal and distal ends, an inner lumen extending therethrough and at least one outlet port formed therein and configured to deliver fluid to surrounding tissue. The device can also include at least one ablation element disposed along a length of the body adjacent to the at least one outlet port and configured to deliver energy to surrounding tissue, as well as at least one heating element disposed within the inner lumen of the elongate body. The device further includes a handle having proximal and distal ends, the distal end of the handle being coupled to the proximal end of the elongate body. Further, a longitudinal axis of the elongate body extends at an angle to a longitudinal axis of the handle.

30 Claims, 10 Drawing Sheets

(58) Field of Classification Search
CPC .............. A61B 18/148; A61B 18/22; A61B 2017/00247; A61B 2017/00
See application file for complete search history.

(56) References Cited

U.S. PATENT DOCUMENTS

| | | |
|---|---|---|
| 5,271,413 A | 12/1993 | Dalamagas et al. |
| 5,336,222 A | 8/1994 | Durgin, Jr. et al. |
| 5,403,311 A | 4/1995 | Abele et al. |
| 5,409,487 A | 4/1995 | Jalbert et al. |
| 5,431,648 A | 7/1995 | Lev |
| 5,431,649 A | 7/1995 | Mulier et al. |
| 5,437,629 A | 8/1995 | Goldrath |
| 5,437,673 A | 8/1995 | Baust et al. |
| 5,449,380 A | 9/1995 | Chin |
| 5,456,682 A | 10/1995 | Edwards et al. |
| 5,458,597 A | 10/1995 | Edwards et al. |
| 5,462,521 A | 10/1995 | Brucker et al. |
| 5,472,441 A | 12/1995 | Edwards et al. |
| 5,496,271 A | 3/1996 | Burton et al. |
| 5,522,815 A | 6/1996 | Durgin, Jr. et al. |
| 5,545,195 A | 8/1996 | Lennox et al. |
| 5,549,559 A | 8/1996 | Eshel |
| 5,609,151 A | 3/1997 | Mulier et al. |
| 5,653,692 A | 8/1997 | Masterson et al. |
| 5,728,143 A | 3/1998 | Gough et al. |
| 5,735,846 A | 4/1998 | Panescu et al. |
| 5,800,482 A | 9/1998 | Pomeranz et al. |
| 5,827,269 A | 10/1998 | Saadat |
| 5,891,094 A | 4/1999 | Masterson et al. |
| 5,891,134 A | 4/1999 | Goble et al. |
| 5,944,713 A | 8/1999 | Schuman |
| 5,954,719 A | 9/1999 | Chen et al. |
| 5,964,791 A | 10/1999 | Bolmsjo |
| 6,024,743 A | 2/2000 | Edwards |
| 6,030,379 A | 2/2000 | Panescu et al. |
| 6,032,077 A | 2/2000 | Pomeranz |
| 6,033,383 A | 3/2000 | Ginsburg |
| 6,045,549 A | 4/2000 | Smethers et al. |
| 6,056,746 A | 5/2000 | Goble et al. |
| 6,071,280 A | 6/2000 | Edwards et al. |
| 6,080,151 A | 6/2000 | Swartz et al. |
| 6,090,106 A | 7/2000 | Goble et al. |
| 6,112,123 A | 8/2000 | Kelleher et al. |
| 6,119,041 A | 9/2000 | Pomeranz et al. |
| 6,139,570 A | 10/2000 | Saadat et al. |
| 6,139,571 A | 10/2000 | Fuller et al. |
| 6,179,803 B1 | 1/2001 | Edwards et al. |
| 6,208,881 B1 | 3/2001 | Champeau |
| 6,233,490 B1 | 5/2001 | Kasevich |
| 6,238,393 B1 | 5/2001 | Mulier et al. |
| 6,272,370 B1 | 8/2001 | Gillies et al. |
| 6,302,904 B1 | 10/2001 | Wallsten et al. |
| 6,315,777 B1 | 11/2001 | Comben |
| 6,328,735 B1 * | 12/2001 | Curley .................. A61B 18/04 606/14 |
| 6,337,994 B1 | 1/2002 | Stoianovici et al. |
| 6,358,273 B1 | 3/2002 | Strul et al. |
| 6,405,067 B1 | 6/2002 | Mest et al. |
| 6,409,722 B1 | 6/2002 | Hoey et al. |
| 6,411,852 B1 | 6/2002 | Danek et al. |
| 6,443,947 B1 | 9/2002 | Marko et al. |
| 6,463,332 B1 | 10/2002 | Aldrich |
| 6,464,694 B1 | 10/2002 | Massengill |
| 6,468,274 B1 | 10/2002 | Alleyne et al. |
| 6,475,213 B1 | 11/2002 | Whayne et al. |
| 6,477,396 B1 | 11/2002 | Mest et al. |
| 6,494,902 B2 | 12/2002 | Hoey et al. |
| 6,529,756 B1 | 3/2003 | Phan et al. |
| 6,564,096 B2 | 5/2003 | Mest |
| 6,565,561 B1 | 5/2003 | Goble et al. |
| 6,603,997 B2 | 8/2003 | Doody |
| 6,620,155 B2 | 9/2003 | Underwood et al. |
| 6,641,580 B1 | 11/2003 | Edwards et al. |
| 6,669,685 B1 | 12/2003 | Rizoiu et al. |
| 6,678,552 B2 | 1/2004 | Pearlman |
| 6,702,810 B2 * | 3/2004 | McClurken ............ A61B 18/14 606/34 |
| 6,752,802 B1 | 6/2004 | Isenberg et al. |
| 6,772,012 B2 | 8/2004 | Woloszko et al. |
| 6,814,730 B2 | 11/2004 | Li |
| 6,904,303 B2 | 6/2005 | Phan et al. |
| 6,972,014 B2 | 12/2005 | Eum et al. |
| 7,001,378 B2 | 2/2006 | Yon et al. |
| 7,070,597 B2 | 7/2006 | Truckai et al. |
| 7,101,369 B2 | 9/2006 | van der Welde |
| 7,160,259 B2 | 1/2007 | Tardy et al. |
| 7,179,256 B2 | 2/2007 | Mest |
| 7,207,989 B2 | 4/2007 | Pike, Jr. et al. |
| 7,244,254 B2 | 7/2007 | Brace et al. |
| 7,270,659 B2 | 9/2007 | Ricart et al. |
| 7,311,703 B2 | 12/2007 | Turovskiy et al. |
| 7,387,625 B2 | 6/2008 | Hovda et al. |
| 7,387,630 B2 | 6/2008 | Mest |
| 7,412,273 B2 | 8/2008 | Jais et al. |
| 7,416,552 B2 | 8/2008 | Paul et al. |
| 7,559,905 B2 | 7/2009 | Kagosaki et al. |
| 7,604,634 B2 | 10/2009 | Hooven |
| 7,879,030 B2 | 2/2011 | Paul et al. |
| 7,938,822 B1 | 5/2011 | Berzak et al. |
| 7,951,143 B2 | 5/2011 | Wang et al. |
| 7,993,335 B2 | 8/2011 | Rioux et al. |
| 8,128,620 B2 | 3/2012 | Wang et al. |
| 8,128,621 B2 | 3/2012 | Wang et al. |
| 8,273,082 B2 | 9/2012 | Wang et al. |
| 8,287,531 B2 | 10/2012 | Mest |
| 8,333,762 B2 | 12/2012 | Mest et al. |
| 8,369,922 B2 | 2/2013 | Paul et al. |
| 8,439,907 B2 | 5/2013 | Auth et al. |
| 8,444,638 B2 | 5/2013 | Woloszko et al. |
| 8,449,535 B2 | 5/2013 | Deno et al. |
| 8,515,560 B2 | 8/2013 | Debruyne et al. |
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 9,610,396 B2 | 4/2017 | Curley et al. |
| 9,730,748 B2 | 8/2017 | Curley |
| 9,743,984 B1 | 8/2017 | Curley et al. |
| 2001/0031946 A1 | 10/2001 | Walker et al. |
| 2002/0120259 A1 | 8/2002 | Lettice et al. |
| 2002/0123749 A1 | 9/2002 | Jain |
| 2002/0153046 A1 | 10/2002 | Dantsker et al. |
| 2002/0183735 A1 | 12/2002 | Edwards et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 | 6/2004 | Hovda et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0165391 A1 | 7/2005 | Maguire et al. |
| 2005/0187599 A1 * | 8/2005 | Sharkey et al. ............... 607/98 |
| 2005/0192652 A1 | 9/2005 | Cioanta et al. |
| 2005/0245923 A1 | 11/2005 | Christopherson et al. |
| 2005/0267552 A1 * | 12/2005 | Conquergood et al. ........ 607/96 |
| 2006/0085054 A1 | 4/2006 | Zikorus et al. |
| 2006/0118127 A1 | 6/2006 | Chinn |
| 2006/0129091 A1 | 6/2006 | Bonnette et al. |
| 2006/0216275 A1 | 9/2006 | Mon |
| 2006/0259024 A1 | 11/2006 | Turovskiy et al. |
| 2006/0276780 A1 | 12/2006 | Brace et al. |

(56) References Cited

U.S. PATENT DOCUMENTS

| | | |
|---|---|---|
| 2006/0287650 A1 | 12/2006 | Cao et al. |
| 2007/0027448 A1 | 2/2007 | Paul et al. |
| 2007/0032786 A1 | 2/2007 | Francischelli |
| 2007/0167775 A1 | 7/2007 | Kochavi et al. |
| 2007/0185483 A1 | 8/2007 | Butty et al. |
| 2007/0219434 A1 | 9/2007 | Abreu |
| 2007/0250056 A1 | 10/2007 | Vanney |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161797 A1 | 7/2008 | Wang et al. |
| 2008/0167650 A1 | 7/2008 | Joshi et al. |
| 2008/0249463 A1 | 10/2008 | Pappone et al. |
| 2008/0275438 A1 | 11/2008 | Gadsby et al. |
| 2008/0275440 A1 | 11/2008 | Kratoska et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1* | 7/2009 | Luttich ............ A61B 18/1477 606/41 |
| 2009/0254083 A1 | 10/2009 | Wallace et al. |
| 2010/0030098 A1 | 2/2010 | Fojtik |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1* | 3/2011 | Cheng ............. A61B 17/0401 606/139 |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1 | 11/2011 | Clark et al. |
| 2011/0282342 A1 | 11/2011 | Leo et al. |
| 2012/0108938 A1 | 5/2012 | Kauphusman et al. |
| 2012/0130381 A1 | 5/2012 | Germain |
| 2012/0165812 A1 | 6/2012 | Christian |
| 2012/0265190 A1* | 10/2012 | Curley .............. A61B 18/082 606/28 |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2014/0058386 A1 | 2/2014 | Clark et al. |
| 2014/0188106 A1 | 7/2014 | Curley |
| 2014/0275977 A1 | 9/2014 | Curley et al. |
| 2014/0276743 A1 | 9/2014 | Curley |
| 2014/0276758 A1 | 9/2014 | Lawrence et al. |
| 2014/0350542 A1 | 11/2014 | Kramer et al. |
| 2015/0066025 A1 | 3/2015 | Curley |
| 2015/0223882 A1 | 8/2015 | Curley |
| 2015/0351823 A1 | 12/2015 | Curley |
| 2015/0359582 A1 | 12/2015 | Curley et al. |
| 2016/0354138 A1 | 12/2016 | Curley |
| 2017/0238993 A1 | 8/2017 | Curley |
| 2017/0296739 A1 | 10/2017 | Curley et al. |
| 2017/0333107 A1 | 11/2017 | Curley |

FOREIGN PATENT DOCUMENTS

| | | |
|---|---|---|
| CN | 1525839 A | 9/2004 |
| CN | 1897885 A | 1/2007 |
| CN | 101209217 A | 7/2008 |
| CN | 101578073 A | 11/2009 |
| CN | 101773699 A | 7/2010 |
| CN | 201642316 U | 11/2010 |
| CN | 101999931 A | 4/2011 |
| EP | 0 895 756 A1 | 2/1999 |
| EP | 0 908 156 A1 | 4/1999 |
| EP | 1 033 107 A1 | 9/2000 |
| EP | 2 042 112 A2 | 4/2009 |
| EP | 2 430 996 A2 | 3/2012 |
| JP | 10-505268 A | 5/1998 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/32186 A1 | 7/1999 |
| WO | 02/089686 A1 | 11/2002 |
| WO | 2005/048858 A1 | 6/2005 |
| WO | 2005/089663 A1 | 9/2005 |
| WO | 2006/055658 A1 | 5/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2010/002733 A1 | 1/2010 |
| WO | 2010/151619 A2 | 12/2010 |
| WO | 2012/071058 A1 | 5/2012 |

OTHER PUBLICATIONS

Brace CL. Microwave tissue ablation: biophysics, technology, and applications.; Crit Rev Biomed Eng. 2010;38 (1):65-78.
International Search Report and Written Opinion for Application No. PCT/US2014/024731, mailed Jul. 21, 2014 (39 pages).
Extended Search Report and Written Opinion for EP 12 77 0537 dated Oct. 10, 2014 (6 pages).
Extended Search Report and Written Opinion for EP 12 77 0631.5 dated Oct. 1, 2014 (6 Pages).
Extended Search Report and Written Opinion for EP 12 77 1331.1 dated Sep. 25, 2014 (6 Pages).
Extended Search Report and Written Opinion for EP 12 77 1876 dated Oct. 13, 2014 (6 pages).
Extended European Search Report and Written Opinion for Application No. 12771601.7 issued Oct. 27, 2014 (7 pages).
David R. Lide (ed)., CRC Handbook of Chemistry and Physics, 87th Edition. 2006. p. 8-81. CRC Press, Florida.
International Search Report and Written Opinion for Application No. PCT/US2012/033203, issued Sep. 21, 2012. (23 pages).
International Search Report and Written Opinion for Application No. PCT/US2012/033213, issued Sep. 21, 2012. (17 pages).
International Search Report and Written Opinion for Application No. PCT/US2012/033216, issued Sep. 21, 2012. (17 pages).
International Search Report and Written Opinion for Application No. PCT/US2012/033327, issued Sep. 21, 2012. (14 pages).
International Search Report and Written Opinion for Application No. PCT/US2012/033332, issued Sep. 21, 2012. (20 pages).
Nath et al., Prog. Card. Dis. 37(4):185-205 (1995).
Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.
Sapareto et al., Int. J Rad. One. Biol. Phys. 10(6):787-800 (1984).
Chinese Office Action for Application No. 201280028609.9, issued May 27, 2015. (22 pages).
Chinese Office Action for Application No. 201280028620.5, issued May 27, 2015. (26 pages).
Chinese Office Action for Application No. 2012800286116, issued Jul. 29, 2015 (23 pages).
Chinese Office Action for Application No. 201280028621.X, issued Jul. 31, 2015. (18 pages).
Extended European Search Report and Search Opinion for Application No. 13829821.1 issued Mar. 17, 2016 (7 pages).
Japanese Office Action for Application No. 2014-505263, mailed Jan. 26, 2016 (4 pages).
Japanese Office Action for Application No. 2014-505266, mailed Feb. 23, 2016 (7 pages).

(56) References Cited

OTHER PUBLICATIONS

Young, S.T., et al., An instrument using variation of resistance to aid in needle tip insertion in epidural block in monkeys. Med Instrum. Oct. 1987;21(5):266-8. Abstract Only.

Chinese Office Action for Application No. 201380053690.0, issued Sep. 30, 2016. (17 pages).

U.S. Appl. No. 15/240,693, filed Aug. 18, 2016, Methods and Devices for Controlling Ablation Therapy.

U.S. Appl. No. 14/688,790, filed Apr. 16, 2015, Methods and Devices for Fluid Enhanced Microwave Ablation Therapy.

U.S. Appl. No. 14/826,549, filed Aug. 14, 2015, Methods and Devices for Heating Fluid in Fluid Enhanced Ablation Therapy.

U.S. Appl. No. 14/826,563, filed Aug. 14, 2015, Methods and Devices for Use of Degassed Fluids With Fluid Enhanced Ablation Devices.

U.S. Appl. No. 14/536,212, filed Nov. 7, 2014, Methods and Devices for Use of Degassed Fluids With Fluid Enhanced Ablation Devices.

U.S. Appl. No. 15/234,858, filed Aug. 11, 2016, Devices and Methods for Delivering Fluid to Tissue During Ablation Therapy.

U.S. Appl. No. 13/445,036, filed Apr. 12, 2012, Methods and Devices for Heating Fluid in Fluid Enhanced Ablation Therapy.

U.S. Appl. No. 13/445,365, filed Apr. 12, 2012, Devices and Methods for Shaping Therapy in Fluid Enhanced Ablation.

U.S. Appl. No. 13/445,040, filed Apr. 12, 2012, Methods and Devices for Use of Degassed Fluids With Fluid Enhanced Ablation Devices.

U.S. Appl. No. 13/445,373, filed Apr. 12, 2012, Methods and Devices for Controlling Ablation Therapy.

U.S. Appl. No. 13/445,034, filed Apr. 12, 2012, Devices and Methods for Remote Temperature Monitoring in Fluid Enhanced Ablation Therapy.

U.S. Appl. No. 13/837,295, filed Mar. 15, 2013, Methods and Devices for Fluid Enhanced Microwave Ablation Therapy.

U.S. Appl. No. 13/842,561, filed Mar. 15, 2013, Systems and Methods for Visualizing Fluid Enhanced Ablation Therapy.

U.S. Appl. No. 14/202,425, filed Mar. 10, 2014, Devices and Methods for Shaping Therapy in Fluid Enhanced Ablation.

Chinese Office Action for Application No. 201280028612.0, dated Nov. 2, 2016. (8 pages).

Chinese Office Action for Application No. 201380053690.0, dated Jul. 20, 2017. (18 pages).

International Search Report and Written Opinion for Application No. PCT/US2017/044706, dated Nov. 29, 2017 (25 pages).

\* cited by examiner

LOW PROFILE FLUID ENHANCED ABLATION THERAPY DEVICES AND METHODS

FIELD

This application relates generally to fluid enhanced ablation therapy, and more particularly, this application relates to improved low profile devices and methods for administering fluid enhanced ablation therapy.

BACKGROUND

The use of thermal energy to destroy bodily tissue can be applied to a variety of therapeutic procedures, including the destruction of tumors. Thermal energy can be imparted to the tissue using various forms of energy, such as radio frequency electrical energy, microwave or light wave electromagnetic energy, or ultrasonic vibrational energy. Radio frequency (RF) ablation, for example, can be effected by placing one or more electrodes against or into tissue to be treated and passing high frequency electrical current into the tissue. The current can flow between closely spaced emitting electrodes or between an emitting electrode and a larger, common electrode located remotely from the tissue to be heated.

One disadvantage with these techniques is that maximum heating often occurs at or near the interface between the therapeutic tool and the tissue. In RF ablation, for example, maximum heating can occur in the tissue immediately adjacent to the emitting electrode. This can reduce the conductivity of the tissue, and in some cases, can cause water within the tissue to boil and become water vapor. As this process continues, the impedance of the tissue can increase and prevent current from entering into the surrounding tissue. Thus, conventional RF instruments are limited in the volume of tissue that can be treated.

Fluid enhanced ablation therapy, such as the SERF™ ablation technique (Saline Enhanced Radio Frequency™ ablation), can treat a greater volume of tissue than conventional RF ablation. The SERF ablation technique is described in U.S. Pat. No. 6,328,735, which is hereby incorporated by reference in its entirety. Using the SERF ablation technique, saline is passed through a needle and heated, and the heated fluid is delivered to the tissue immediately surrounding the needle. The saline helps distribute the heat developed adjacent to the needle and thereby allows a greater volume of tissue to be treated with a therapeutic dose of ablative energy. The therapy is usually completed once a target volume of tissue reaches a desired therapeutic temperature, or otherwise receives a therapeutic dose of energy.

Fluid enhanced ablation therapy can be administered to a patient in a variety of manners. For example, an RF electrode can be introduced into a patient's body percutaneously using a needle during a laparoscopic or other minimally invasive surgical procedure. In such a procedure, a surgeon, doctor, interventional radiologist, or other medical professional administering the therapy must utilize a medical imaging apparatus to guide the positioning of the RF electrode at a desired location. Such an imaging apparatus can also be utilized to monitor the effectiveness of the therapy as the procedure progresses.

Many medical imaging apparatuses, however, require a patient to be placed in a space-constrained volume within the apparatus in order to be effectively imaged. X-ray Computed Tomography (CT) scanners and Magnetic Resonance Imaging (MRI) scanners, for example, often require a patient to be moved through a small cylindrical opening in the device. Moving a patient through these devices while long needles and extended manipulating handles are protruding from their body can be difficult or impossible. Professionals administering the therapy can be forced to remove the devices from the patient and subsequently reintroduce them several times in order to successfully image and treat the targeted area of the patient's body.

Accordingly, there is a need for improved low profile fluid enhanced ablation therapy devices and methods that can be utilized by medical professionals in space-constrained environments, such as within medical imaging apparatuses.

SUMMARY

The present invention generally provides low profile devices and methods for administering fluid enhanced ablation therapy. In particular, the devices and methods described herein permit surgeons, doctors, radiologists, or other medical professionals to administer fluid enhanced ablation therapy in space-constrained environments, such as inside medical imaging apparatuses. The low profile devices and methods of the present invention can thereby allow continuous or periodic medical imaging of the ablation therapy to determine positional accuracy and therapy effectiveness without having to remove and re-introduce any ablation devices being used.

In one aspect, an ablation device is provided that includes an elongate body having proximal and distal ends, an inner lumen extending longitudinally through the elongate body, and at least one outlet port formed in the elongate body and configured to deliver fluid to tissue surrounding the elongate body. The ablation device further includes at least one ablation element disposed along a length of the elongate body adjacent to the at least one outlet port and configured to deliver energy to tissue surrounding the elongate body. The ablation device also includes a handle having proximal and distal ends, the distal end of the handle being coupled to the proximal end of the elongate body. In addition, a longitudinal axis of the elongate body can extend at an angle to a longitudinal axis of the handle.

The devices and methods described herein can have a variety of modifications and additional features, all of which are considered within the scope of the invention. For example, in some embodiments, the angle between the longitudinal axis of the elongate body and the longitudinal axis of the handle can be about 90 degrees. In other embodiments, the angle can be acute, or less than 90 degrees, such that the handle extends at least partially back towards the distal end of the elongate body. In still other embodiments, the angle can be obtuse, or greater than 90 degrees, such that the handle extends proximally and farther away from the distal end of the elongate body. In certain embodiments, for example, the angle between the longitudinal axis of the elongate body and the longitudinal axis of the handle can be in a range of about 10 degrees to about 120 degrees. In other embodiments, the angle can be in a range of about 30 degrees to about 100 degrees, and in still other embodiments the and can be in a range of about 45 degrees to about 90 degrees.

In certain embodiments, the handle can include an inner lumen extending therethrough that can be used to transport fluid and/or electrical power to the distal end of the elongate body. As a result, in some embodiments, the inner lumen of the handle can be in communication with the inner lumen of the elongate body.

The handle itself can have a variety of shapes and sizes. For example, in some embodiments the handle can be straight along its longitudinal length. In other embodiments, however, the handle can be contoured along its longitudinal length to better fit within a user's hand. Such contouring can also be present in other directions as well (e.g., along a circumference or width of the handle) to enable a user to more comfortably and accurately manipulate the ablation device. The size of the handle can also be varied according to preference to fit a user's hand by, for example, making the handle longer, thicker, and heavier, or smaller, thinner, and lighter, etc. In other embodiments, the handle can include a surface texture or other surface features to improve a user's grip of the device. This can be especially useful if the user is wearing surgical gloves or has come into contact with one or more bodily or cleansing fluids.

As a result of the fact that the handle is coupled to an elongate body that can be inserted percutaneously into a patient's body, the ablation device can also include an insertion stopping element slidably disposed on the elongate body to prevent over-insertion of the device.

In some embodiments, the entire ablation device can be formed from materials that are non-magnetic (i.e., negligibly affected by or affecting magnetic fields). Forming the device from non-magnetic materials can allow the device to remain in a patient when imaged using, for example, Magnetic Resonance Imaging (MRI) scanners that create strong magnetic fields as part of the imaging process.

In certain embodiments, the ablation device can further include at least one heating element disposed within the inner lumen of the elongate body and configured to heat fluid passing therethrough. The introduction of therapeutically heated fluid into tissue surrounding the distal end of the elongate body can have several advantages, as is described in more detail below. The at least one heating element can have a variety of forms but, in one embodiment, a heating element can include at least one wire and at least one spacer where the at least one wire is configured to pass energy through the fluid flowing through the inner lumen of the elongate body. By passing energy through the fluid within the inner lumen of the elongate body, the fluid's temperature can be increased due to its natural resistance. The at least one spacer can be used to maintain the position of the at least one wire within the inner lumen of the elongate body.

In another aspect, a method for administering fluid enhanced ablation therapy is provided that includes percutaneously inserting a distal end of an elongate body of an ablation device into a patient. The method further includes manipulating the distal end of the elongate body within the patient using a low profile handle coupled to the proximal end of the elongate body and having a longitudinal axis that extends at an angle to a longitudinal axis of the elongate body. The method further includes delivering fluid through the elongate body of the ablation device into tissue surrounding the distal end of the elongate body while simultaneously delivering energy into tissue surrounding the distal end of the elongate body.

In some embodiments, the method can further include imaging at least a portion of the patient using a medical imaging apparatus. Furthermore, in some embodiments, imaging can occur simultaneously with any of the manipulating step and the delivering step. Accordingly, in some embodiments, the patient can be positioned within the medical imaging apparatus during at least a portion of the method. Indeed, in some embodiments, both the manipulating step and the delivering step can be performed inside the medical imaging apparatus.

Any of a number of medical imaging apparatuses can be utilized in the methods disclosed herein. For example, in some embodiments the imaging apparatus can be selected from the group consisting of an X-ray Computed Tomography (CT) scanner, a Magnetic Resonance Imaging (MRI) scanner, an ultrasound scanner, and an X-ray scanner. However, other imaging devices known in the prior art can also be utilized with the methods of the present invention.

In certain embodiments, the method can further include heating the fluid inside the elongate body prior to delivering the fluid into the tissue surrounding the elongate body. As mentioned above and discussed in more detail below, heating the fluid prior to delivery into tissue can be beneficial and enhance the effectiveness of the fluid enhanced ablation therapy.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Figure 1:
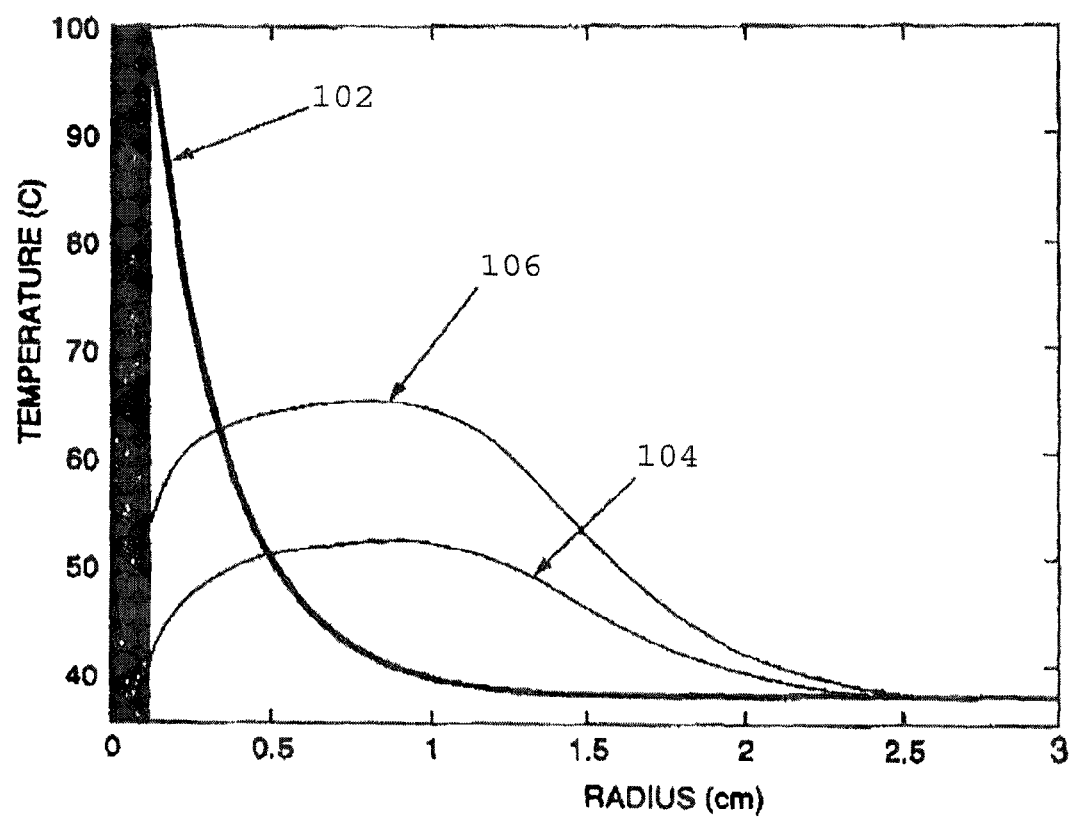
FIG. 1 is a graphical representation of simulated heating profiles for various forms of ablation.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,")

unless otherwise noted. The terms "about" and "approximately" used for any numerical values or ranges indicate a suitable dimensional tolerance that allows the composition, part, or collection of elements to function for its intended purpose as described herein. These terms generally indicate a ±10% variation about a central value. Components described herein as being coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention. Further, to the extent the term "saline" is used in conjunction with any embodiment herein, such embodiment is not limited to the use of "saline" as opposed to another fluid unless explicitly indicated. Other fluids can typically be used in a similar manner.

The present invention is generally directed to low profile fluid enhanced ablation devices and methods. These low profile devices and methods allow for the administration of fluid enhanced ablation therapy in space-constrained environments, such as within a medical imaging apparatus (e.g., a Magnetic Resonance Imaging, or MRI, scanner, etc.). The low profile devices and methods disclosed herein generally accommodate more tightly constrained environments by including handles for manipulating the devices that extend at an angle to the needles or other elongate bodies that are inserted into a patient's body to administer the therapy. By extending a handle in a direction that is offset from a longitudinal axis of the elongate body inserted into a patient, the required clearance space surrounding the patient's body can be reduced.

Fluid enhanced ablation therapy, as mentioned above, is defined by passing a fluid into tissue while delivering therapeutic energy from an ablation element. The delivery of therapeutic energy into tissue causes hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others.

The SERF™ ablation technique (Saline Enhanced Radio Frequency™ ablation) described in U.S. Pat. No. 6,328,735 and incorporated by reference above, delivers fluid heated to a therapeutic temperature into tissue along with ablative energy. Delivering heated fluid enhances the ablation treatment because the fluid flow through the extracellular space of the treatment tissue can increase the heat transfer through the tissue significantly. The flowing heated fluid therefore convects thermal energy from the ablation energy source further into the target tissue. In addition, the fact that the fluid is heated to a therapeutic temperature increases the amount of energy that can be imparted into the tissue. Finally, the fluid can also serve to constantly hydrate the tissue and prevent any charring and associated impedance rise, as described in more detail below.

By way of illustration, ablation is often quantified in terms of an administered thermal dose level, which can be expressed as a particular time during which tissue was raised to a temperature above 41° Celsius (C) (a generally accepted threshold temperature for causing irreversible damage to tissue). A number of different methods exist for determining a therapeutic thermal dose, but Nath, S. and Haines, D. E., Prog. Card. Dis. 37(4):185-205 (1995) (Nath et al.) suggest a temperature of 50° C. for one minute as therapeutic. Using this as a reference, FIG. 1 shows the performance profiles of several ablation techniques by plotting a simulated temperature profile achieved as a function of distance from an ablation element, such as an emitter electrode. The first profile 102 illustrates the performance of RF ablation without the use of fluid enhancement. As shown in the figure, the temperature of the tissue falls very sharply with distance from the electrode. This means that within 10 mm of the ablation element the temperature of the tissue is still approximately body temperature (37° C.), far below the therapeutic temperature of 50° C. mentioned above. Furthermore, very close to the ablation element the temperature is very high, meaning that the tissue will more quickly desiccate, or dry up, and char. Once this happens, the impedance of the tissue rises dramatically, making it difficult to pass energy to tissue farther away from the ablation element.

A second tissue temperature profile 104 is associated with a second prior art system similar to that described in U.S. Pat. No. 5,431,649. In this second system, an electrode is inserted into tissue and imparts a 400 kHz RF current flow of about 525 mA to heat the tissue. Body temperature (37° C.) saline solution is simultaneously injected into the tissue at a rate of 10 ml/min. The resulting tissue temperature profile 104 is more uniform than profile 102, but the maximum temperature achieved anywhere is approximately 50° C. Thus, the temperature profile 104 exceeds the 50° C. temperature threshold specified for one minute of therapy in only a small portion of the tissue. Such a small temperature increment requires significant treatment time to achieve any therapeutically meaningful results.

A third tissue temperature profile 106 is achieved using fluid enhanced ablation therapy. In the illustrated embodiment, an electrode formed from silver/silver chloride is inserted into tissue and imparts a 480 kHz RF current flow of 525 mA to heat the tissue. Saline solution heated to 50° C. is simultaneously injected into the tissue at a rate of 10 ml/min. The resulting temperature profile 106 is both uniform and significantly above the 50° C. therapeutic threshold out to 15 mm from the electrode. Moreover, because the temperature is uniform within the volume, the thermal dose delivered is also uniform through the volume.

The uniform temperature profile seen in FIG. 1 can be achieved by the introduction of heated fluid into the target tissue during application of ablative energy. The fluid convects the heat deeper into the tissue, thereby reducing the charring and impedance change in tissue that occurs near the ablation element, as shown in profile 102. Further, because the fluid is heated to a therapeutic level, it does not act as a heat sink that draws down the temperature of the surrounding tissue, as seen in profile 104. Therefore, the concurrent application of RF energy and perfusion of heated saline solution into the tissue eliminates the desiccation and/or vaporization of tissue adjacent to the electrode, maintains the effective tissue impedance, and increases the thermal transport within the tissue being heated with RF energy. The total volume of tissue that can be heated to therapeutic temperatures is thereby increased. For example, experimental testing has demonstrated that a volume of tissue having a diameter of approximately 8 cm (i.e., a spherical volume of approximately 156 cm$^3$) can be treated in 5 minutes using the fluid enhanced ablation techniques described herein. By comparison, conventional RF can only treat volumes having a diameter of approximately 3 cm (i.e., a spherical volume of approximately 14 cm$^3$) in the same 5-minute timespan.

In addition, fluid enhanced ablation devices have a greater number of parameters that can be varied to adjust the shape of the treatment profile according to the tissue being treated. For example, when using the SERF ablation technique, an operator or control system can modify parameters such as saline temperature (e.g., from about 40° C. to about 80° C.), saline flow rate (e.g., from about 0 ml/min to about 20 ml/min), RF power (e.g., from about 0 W to about 100 W), and duration of treatment (e.g., from about 0 min to about 10 min) to adjust the temperature profile 106. Different electrode configurations can also be used to vary the treatment. For example, an emitter electrode can be configured as a continuous cylindrical band around a needle or other elongate body, or the electrode can be formed in other geometries, such as spherical or helical. The electrode can form a continuous surface area, or it can have a plurality of discrete portions. Still further, the electrode can be adapted for a mono-polar current flow, or multiple electrodes can be configured for bipolar operation, in which one electrode (or a portion of an electrode) acts as a cathode and another electrode (or portion thereof) acts as an anode.

Figure 2:
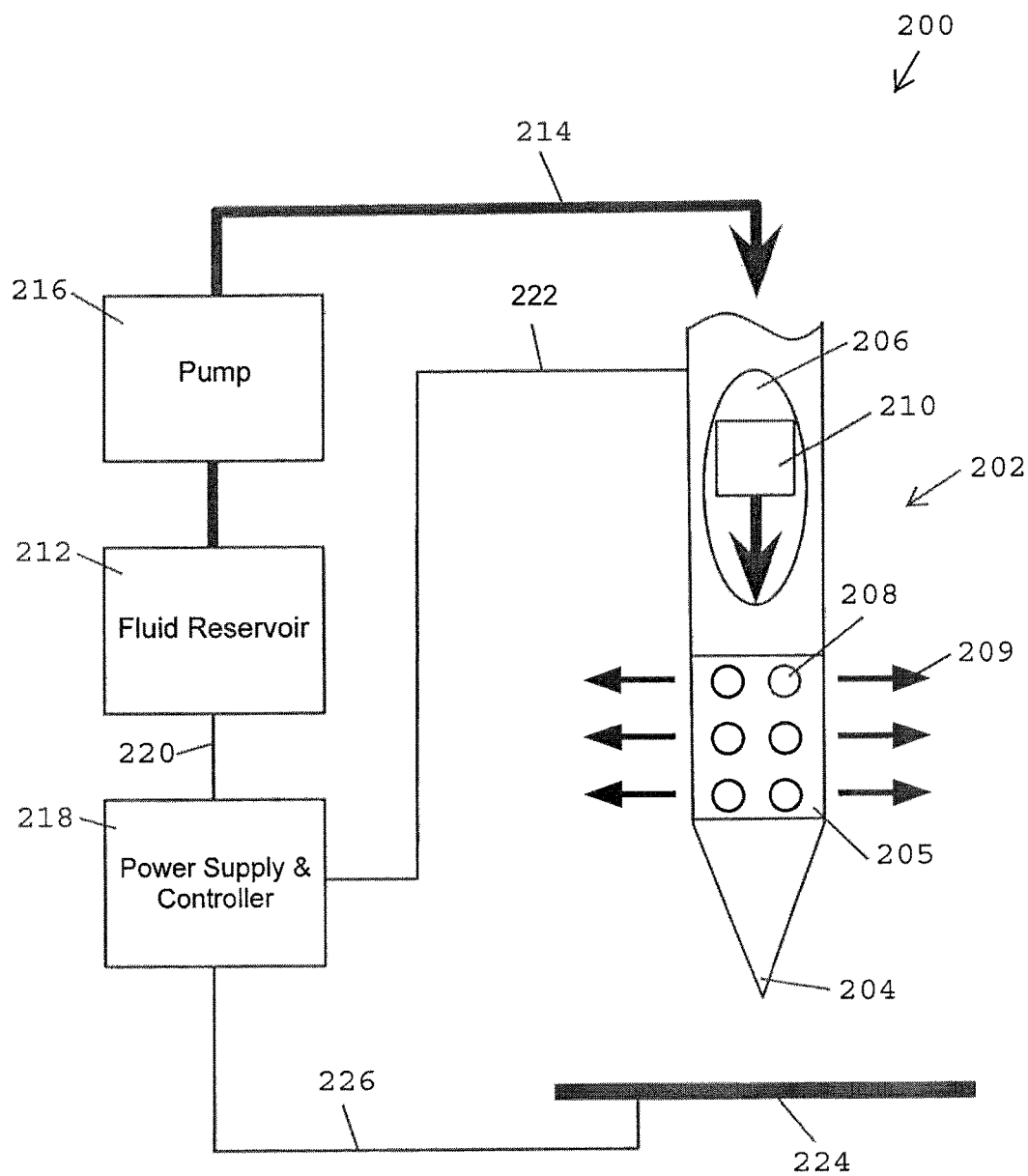
FIG. 2 is a diagram of one embodiment of a fluid enhanced ablation system.
Figure 3:
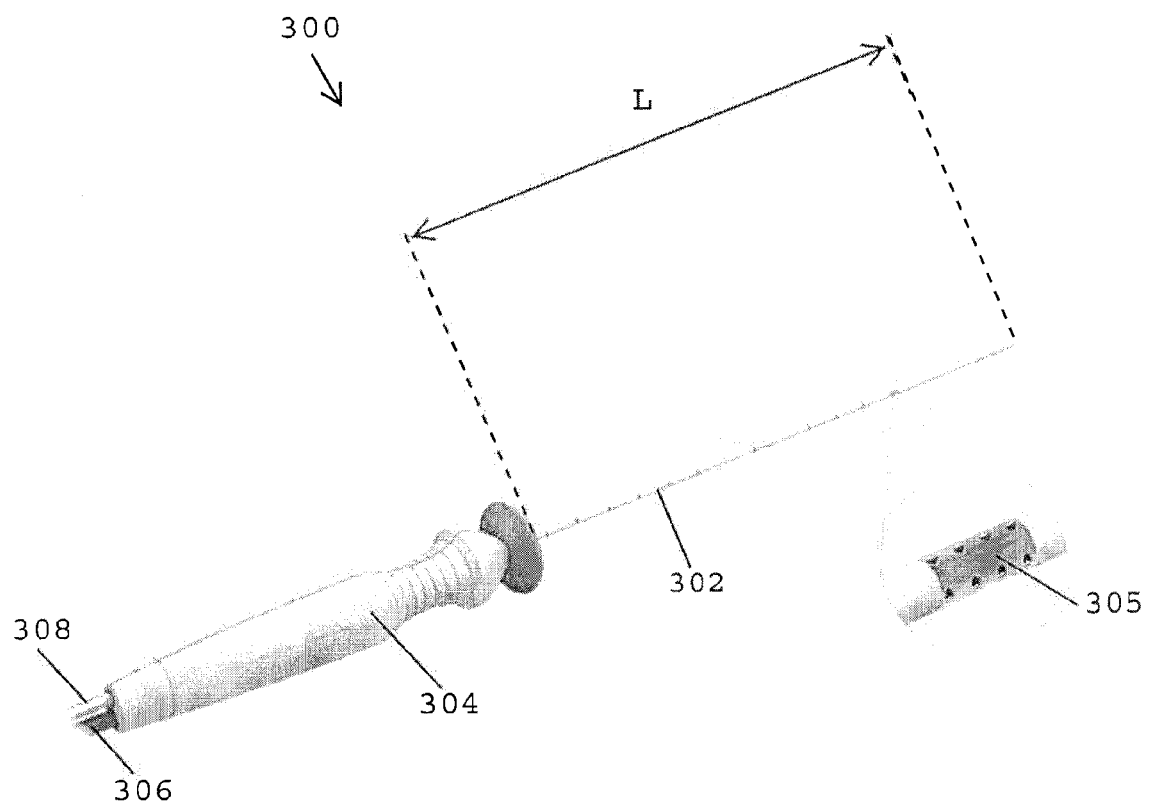
FIG. 3 is a perspective view of a medical device having an elongate body for use in fluid enhanced ablation therapy.

FIG. 2 illustrates a diagram of one embodiment of a fluid enhanced ablation system 100. The system includes an elongate body 202 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and about 18-gauge (i.e., an outer diameter of about 1.27 mm to about 1.65 mm), and having a length L (e.g., as shown in FIG. 3) that is approximately 25 cm. The elongate body 202 can include a pointed distal tip 204 configured to puncture tissue to facilitate introduction of the device into a target volume of tissue, however, in other embodiments the tip can be blunt and can have various other configurations. The elongate body 202 can be formed from a conductive material such that the elongate body can conduct electrical energy along its length to one or more ablation elements located along a distal portion of the elongate body. Emitter electrode 205 is an example of an ablation element capable of delivering RF energy from the elongate body.

In some embodiments, the emitter electrode 205 can be a portion of the elongate body 202. For example, the elongate body 202 can be coated in an insulating material along its entire length except for the portion representing the emitter electrode 205. More particularly, in one embodiment, the elongate body 202 can be coated with 1.5 mil of the fluoropolymer Xylan™ 8840. The electrode 205 can have a variety of lengths and shape configurations. In one embodiment, the electrode 205 can be a 4 mm section of a tubular elongate body that is exposed to surrounding tissue. Further, the electrode 205 can be located anywhere along the length of the elongate body 205 (and there can also be more than one electrode disposed along the length of the elongate body). In one embodiment, the electrode can be located adjacent to the distal tip 204. In other embodiments, the elongate body can be formed from an insulating material, and the electrode can be disposed around the elongate body or between portions of the elongate body.

In other embodiments, the electrode can be formed from a variety of other materials suitable for conducting current. Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

The electrode 205 or other ablation element can include one or more outlet ports 208 that are configured to deliver fluid from an inner lumen 206 extending through the elongate body 202 into surrounding tissue (as shown by arrows 209). Alternatively, the electrode 205 can be positioned near one or more outlet ports 208 formed in the elongate body 202. In many embodiments, it can be desirable to position the electrode adjacent to the one or more outlet ports to maximize the effect of the flowing fluid on the therapy. The outlet ports 208 can be formed in a variety of sizes, numbers, and pattern configurations. In addition, the outlet ports 208 can be configured to direct fluid in a variety of directions with respect to the elongate body 202. These can include the normal orientation (i.e., perpendicular to the elongate body surface) shown by arrows 209 in FIG. 2, as well as orientations directed proximally and distally along a longitudinal axis of the elongate body 202, including various orientations that develop a circular or spiral flow of liquid around the elongate body. Still further, in some embodiments, the elongate body 202 can be formed with an open distal end that serves as an outlet port. By way of example, in one embodiment, twenty-four equally-spaced outlet ports 208 having a diameter of about 0.4 mm can be created around the circumference of the electrode 205 using Electrical Discharge Machining (EDM). One skilled in the art will appreciate that additional manufacturing methods are available to create the outlet ports 208. In addition, in some embodiments, the outlet ports can be disposed along a portion of the elongate body adjacent to the electrode, rather than being disposed in the electrode itself.

The inner lumen 206 that communicates with the outlet ports 208 can also house a heating assembly 210 configured to heat fluid as it passes through the inner lumen 206 just prior to being introduced into tissue. Furthermore, the portion of the elongate body located distal to the electrode 205 or other ablation element can be solid or filled such that the inner lumen 206 terminates at the distal end of the electrode 205. In one embodiment, the inner volume of the portion of the elongate body distal to the electrode can be filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art.

Fluid can be supplied to the inner lumen 206 and heating assembly 210 from a fluid reservoir 212. The fluid reservoir 212 can be connected to the inner lumen 206 via a fluid conduit 214. The fluid conduit 214 can be, for example, a length of flexible plastic tubing. The fluid conduit 214 can also be a rigid tube, or a combination of rigid and flexible tubing. A preferred fluid for use in the SERF ablation technique is sterile normal saline solution (defined as a salt-containing solution). However, other liquids may be used, including Ringer's solution, or concentrated saline solution. A fluid can be selected to provide the desired therapeutic and physical properties when applied to the target tissue and a sterile fluid is recommended to guard against infection of the tissue.

Fluid can be urged from the fluid reservoir 212 into the inner lumen 206 by a pump 216. The pump 216 can be a syringe-type pump that produces a fixed volume flow with advancement of a plunger (not shown). An example of such a pump is a Model 74900 sold by Cole-Palmer Corporation of Chicago, Ill. Other types of pumps, such as a diaphragm pump, may also be employed.

The pump 216 can be controlled by a power supply and controller 218. The power supply and controller 218 can deliver electrical control signals to the pump 216 to cause the pump to produce a desired flow rate of fluid. The power supply and controller 218 can be connected to the pump 216 via an electrical connection 220. The power supply and controller 218 can also be electrically connected to the elongate body 202 via connection 222, and to a collector electrode 224 via connection 226. In addition, the power supply and controller 218 can be connected to the heating assembly 210 through a similar electrical connection, as described below.

The collector electrode 224 can have a variety of forms. For example, the collector electrode 224 can be a large electrode located outside a patient's body. In other embodiments, the collector electrode 224 can be a return electrode located elsewhere along the elongate body 202, or it can be located on a second elongate body introduced into a patient's body at a different location.

In operation, the power supply and controller 218 can drive the delivery of fluid into target tissue at a desired flow rate, the heating of the fluid to a desired therapeutic temperature, and the delivery of therapeutic ablative energy via the one or more ablation elements, such as electrode 205. To do so, the power supply and controller 218 can itself comprise a number of components for generating, regulating, and delivering required electrical control and therapeutic energy signals. For example, the power supply and controller 218 can include one or more frequency generators to create one or more RF signals of a given amplitude and frequency. These signals can be amplified by one or more RF power amplifiers into relatively high-voltage, high-amperage signals, e.g., 50 volts at 1 amp. These RF signals can be delivered to the ablation element via one or more electrical connections 222 and the elongate body 202 such that RF energy is passed between the emitter electrode 205 and the collector electrode 224 that can be located remotely on a patient's body. In embodiments in which the elongate body is formed from non-conductive material, the one or more electrical connections 222 can extend through the inner lumen of the elongate body or along its outer surface to deliver current to the emitter electrode 205. The passage of RF energy between the ablation element and the collector electrode 224 can heat the tissue surrounding the elongate body 202 due to the inherent electrical resistivity of the tissue. The power supply and controller 218 can also include a directional coupler to feed a portion of the one or more RF signals to, for example, a power monitor to permit adjustment of the RF signal power to a desired treatment level.

The elongate body 202 illustrated in FIG. 2 can be configured for insertion into a patient's body in a variety of manners. FIG. 3 illustrates one embodiment of a medical device 300 having an elongate body 302 coupled to a distal end thereof and configured for laparoscopic or direct insertion into a target area of tissue. In addition to the elongate body 302, the device 300 includes a handle 304 to allow an operator to manipulate the device. The handle 304 includes one or more electrical connections 306 that connect various components of the elongate body (e.g., the heating assembly and ablation element 305) to, for example, the power supply and controller 218 described above. The handle 304 also includes at least one fluid conduit 308 for connecting a fluid source to the device 300. In the device 300 shown in FIG. 3, the handle 304 extends from the elongate body 302 along a common longitudinal axis. In other words, the longitudinal axes of the elongate body 302 and the handle 304 are collinear, or at least parallel. Thus, the overall length of the device 300 is the combined longitudinal lengths of the elongate body 302 and handle 304. Furthermore, even more additional overall length may be added to the device as a result of the at least one electrical connection 306 and fluid conduit 308 that can extend along the same longitudinal axis from a proximal end of the handle 304.

The device 300 shown in FIG. 3 can be used in percutaneous or laparoscopic procedures conducted by interventional radiologists or other medical professionals. These procedures can provide fluid enhanced ablation therapy to a large number of regions within the body. However, due to the minimally invasive nature of the procedure (which does not require a large open incision, but rather a small incision for the elongate body 302 to pass through), visualizing the procedure can be difficult for the medical professional administering the therapy. As a result, fluid enhanced ablation therapy is often conducted with the aid of a medical imaging apparatus to visualize the position of the elongate body's distal end within the patient's body, as well as the effectiveness of the therapy.

Figure 4:
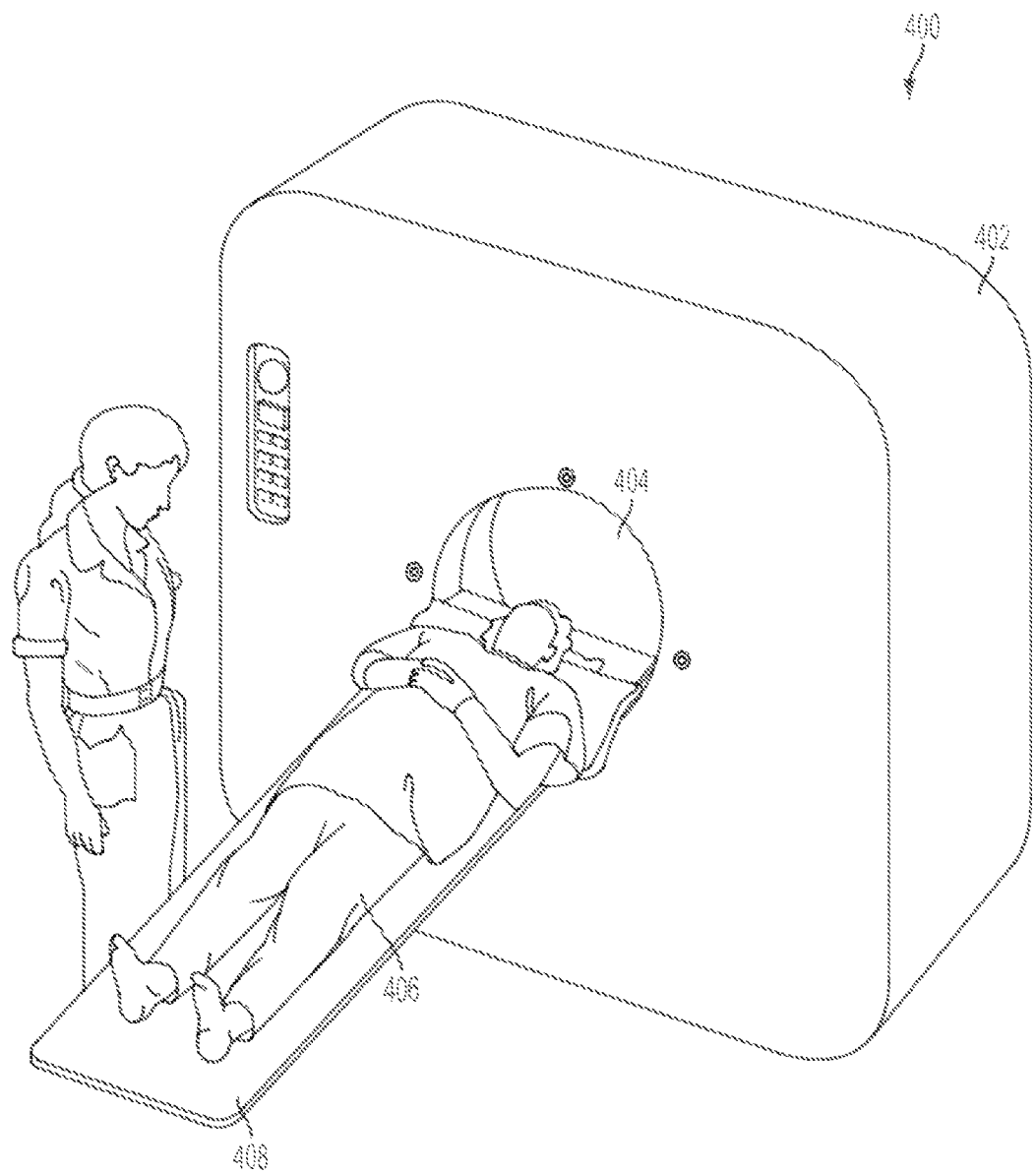
FIG. 4 is an illustration of one embodiment of a medical imaging apparatus.

While different medical facilities have access to different imaging apparatuses, common medical imaging tools employed in combination with fluid enhanced ablation therapy include, for example, X-ray Computed Tomography (CT) scanners, Magnetic Resonance Imaging (MRI) scanners, X-ray scanners, and ultrasound scanners. Several of these scanners, including, for example, CT scanners and MRI scanners, require placing or moving a patient through a space-constrained environment in order to produce an image of the targeted therapy site. FIG. 4, for example, illustrates one embodiment of a CT scanner 400. The CT scanner 400 includes a large scanner housing 402 having a small diameter cylindrical pass-through 404 that is not much larger than a patient 406. The patient 406 is placed on a gurney or sliding tray 408 and subsequently moved back and forth through the pass-through 404. The X-ray computed tomography equipment in the scanner housing 402 rotates around the outer perimeter of the pass-through 404 and collects X-ray images of the patient from a variety of angles. Computer software then analyzes the collected images to construct a model of the patient's body.

One difficulty encountered when using a medical imaging apparatus, such as the CT scanner 400, is that the small diameter pass-through 404 is not large enough to accommodate a patient having one or more devices, such as device 300, protruding from the patient's body. This is the result of the extended length of the device 300. As mentioned above, the fact that the longitudinal axes of the handle 304 and elongate body 302 are parallel or collinear means that the overall length of the device 300 is extended. This greater overall length produces a larger required clearance space around a patient's body. In many situations, the patient cannot be moved through the pass-through 404 of the CT scanner 400 without the handle 304 of the device 300 contacting the scanner housing 402, thereby upsetting the positioning of the device 300.

This potential interference between ablation and imaging components can require the removal of any devices, such as the device 300, that may be protruding from the patient prior to conducting medical imaging. Removing the ablation devices from the patient is undesirable because it can be difficult to reposition the devices correctly and because it can be difficult to gauge the therapy progress if the devices are not visible in the images.

Figure 5:
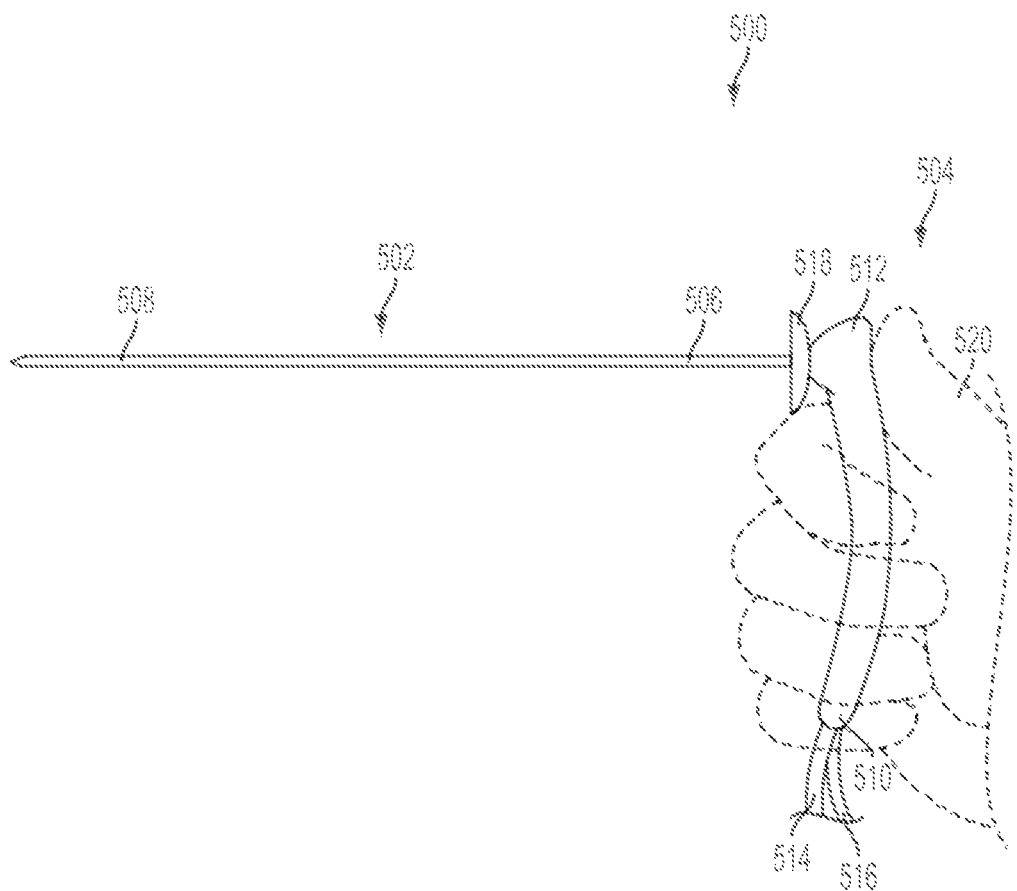
FIG. 5 is a side view of one embodiment of a low profile fluid enhanced ablation device.

To solve these problems, the low profile devices and methods of the present invention include a device manipulation handle that extends at an angle to the longitudinal axis of the elongate body. One embodiment of such a device 500 is illustrated in FIG. 5. The device 500 includes an elongate body 502 and a handle 504 coupled to the elongate body for manipulating it within a patient's body. The elongate body 502 can be similar to the elongate body 202 discussed above. For example, the elongate body 502 can include a proximal end 506, a distal end 508, and an inner lumen extending longitudinally through the elongate body. Furthermore, the elongate body 502 can include at least one ablation element disposed along a length thereof adjacent to one or more outlet ports formed in the elongate body that are configured to deliver fluid into tissue surrounding the elongate body.

The handle 504 can extend between a proximal end 510 and a distal end 512. The distal end 512 of the handle 504 can be coupled to the proximal end 506 of the elongate body 502 such that manipulation of the handle results in corresponding manipulation of the elongate body. Furthermore, the longitudinal axis of the elongate body 502 can extend at an angle α to the longitudinal axis of the handle 504. The angle α formed between the elongate body 502 and the handle 504 can, in some embodiments, be about 90 degrees. Such an angle extends the handle away from the elongate body 502 similar to a pistol grip and minimizes the length of the device 500 along the longitudinal axis of the elongate body 502. In other embodiments, however, the angle α can be acute, or less than 90 degrees, such that the handle extends partially back toward the distal end 508 of the elongate body 502. In still other embodiments, the angle α can be obtuse, or greater than 90 degrees, to ease the severity of the turn that internal conduits must make in routing through the handle into the elongate body. For example, in some embodiments, the angle α can be in a range of about 10 degrees to about 120 degrees, while in other embodiments the angle α can be in a range of about 30 degrees to about 100 degrees. In still other embodiments, the angle α can be in a range of about 45 degrees to about 90 degrees.

Similar to the elongate body 502, the handle 504 can include one or more inner lumens extending therethrough to allow electrical and fluid connections 514, 516 to pass through the handle. To this end, any inner lumens extending through the handle 504 can be in communication with the inner lumen of the elongate body 502.

In some embodiments, the device 500 can also include an insertion stopping element 518 slidably disposed on the elongate body 502. The insertion stopping element 518 can have a larger cross sectional area than the elongate body 502 and can function to prevent over-insertion of the device 500 into a patient's body. The insertion stopping element 518 can be configured to slide along the elongate body but retain its position with an interference fit. In such an embodiment, the insertion stopping element 518 can be set at a variety of adjustable depths and prevent insertion beyond the set depth during a procedure. The insertion stopping element 518 can be formed from a variety of materials, including, for example, rubber or other polymer materials. In certain embodiments, the insertion stopping element can include a flat or concave distal face configured to abut against a patient's skin surface and a sloping proximal face that couples to the distal end 512 of the handle 504.

The handle 504 can have a variety of shapes and sizes depending on the preferences of the user, the size of the elongate body, etc. For example, the handle 504 can be shaped to extend in a straight line between its proximal end 510 and distal end 512. In some embodiments, however, the handle can have a contour along a longitudinal length thereof, as shown in FIG. 5. The contoured shape of the handle can be employed to allow for more comfortable gripping and manipulation by a user's hand 520. With regard to size, the handle can be formed in a variety of sizes but, in some embodiments, can be about 12 cm long and have a width of about 2.5 cm.

Figure 6:
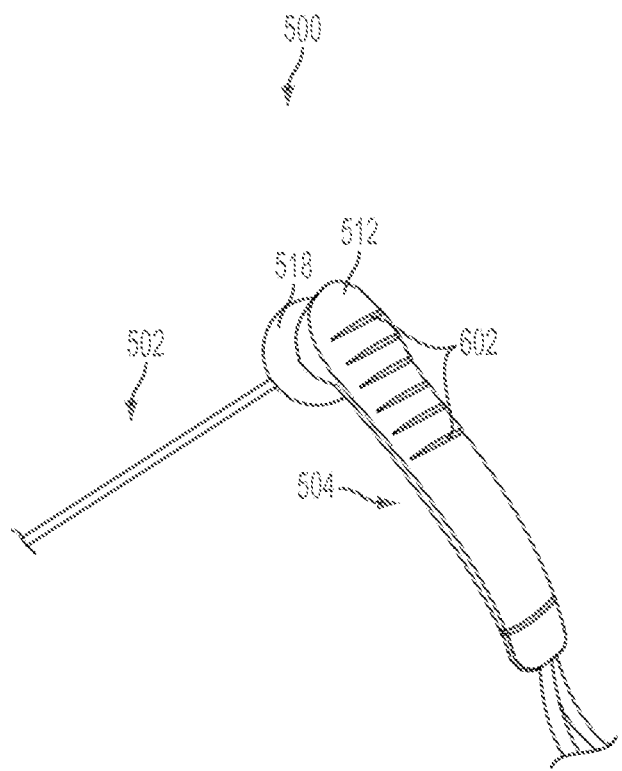
FIG. 6 is an alternate view of the low profile fluid enhanced ablation device of FIG. 5.

In addition to various shapes and sizes, the handle 504 can also include various surface features to enhance the ability of a user to grip and manipulate the device 500. For example, the handle 504 can include a surface texture over a portion or the entirety of the handle, or can include one or more surface texturizing features to aid a user in gripping and manipulating the device 500. For example, FIG. 6 depicts the device 500 from an alternate view and shows a plurality of grooves 602 formed on the surface of the handle 504 near its distal end 512. These grooves can provide a surface that more effectively grips, for example, the thumb of a user's hand 520, as shown in FIG. 5. Such features can be especially beneficial for medical professionals wearing surgical gloves that can become covered in bodily fluids, saline, or other liquids during a procedure.

The handle 504 can be formed from a variety of materials depending on the intended use and required strength, stiffness, and other mechanical properties of the handle. For example, in some embodiments forming the handle (and all other components of the device 500) from a polymer or other non-magnetic material can be preferred so that the device can operate within the strong magnetic fields developed by an MRI scanner. Exemplary non-magnetic materials include, for example, polymers, aluminum, copper, and glass, etc.

Figure 7:
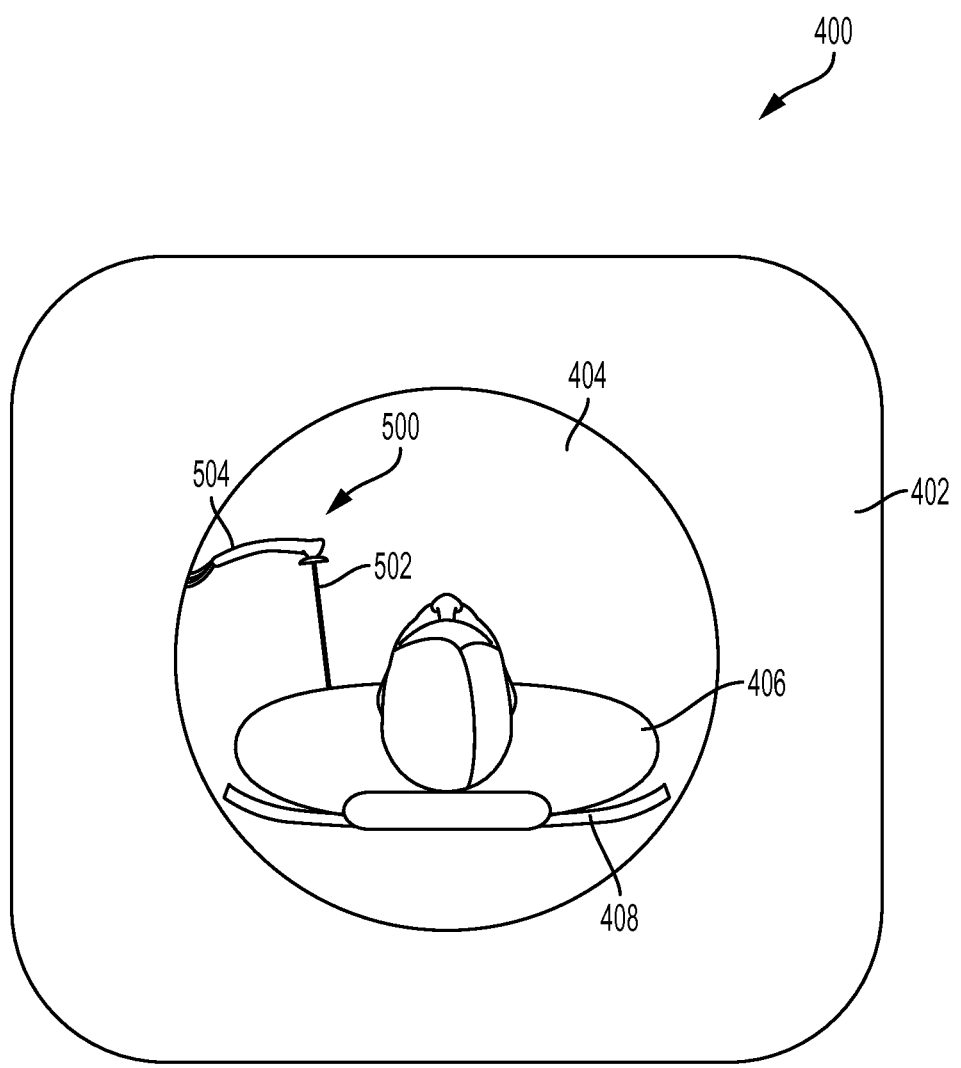
FIG. 7 is a front view of the medical imaging apparatus of FIG. 4 including the low profile fluid enhanced ablation device of FIG. 5.

A low profile handle according to the invention can reduce the overall length of the device 500 such that it can be used in combination with medical imaging devices, such as the CT scanner 400 shown in FIG. 4. FIG. 7 illustrates the reduced clearance space required around a patient when utilizing an ablation device having a handle that extends at an angle to the longitudinal axis of an elongate body inserted into a patient. The figure depicts a front view of the patient 406 being moved through the pass-through 404 in the scanner housing 402 on the sliding tray 408. Inserted into the patient's body is the device 500 described above. The handle 504 of the device 500 extends at an angle to the longitudinal axis of the elongate body 502 and substantially parallel to a skin surface of the patient. As a result, the handle 504 is able to move through the pass-through 404 without interfering with the scanner housing 404, in contrast to the device 200 discussed above.

As mentioned above, the elongate body 502 coupled to the handle 504 can be similar to the elongate body 202 described above and can include, for example, one or more ablation elements disposed along a length thereof and at least one outlet port formed therein for delivering fluid from the inner lumen into tissue surrounding the elongate body. In some embodiments, however, the elongate body can also include at least one heating element disposed within the inner lumen of the elongate body and configured to heat fluid passing therethrough. Heating the fluid prior to its introduction into the tissue surrounding the elongate body can have a number of advantages including, for example, imparting a greater amount of thermal energy into the tissue and preventing the reduction in temperature of the ablation element upon contact therewith, as discussed above. The heating element can have a number of different configurations but, in some embodiments, the heating element can include at least one wire and at least one spacer where the at least one wire is configured to pass energy through the fluid flowing through the inner lumen of the elongate body. By passing energy, e.g., RF electrical energy, through the fluid flowing through the inner lumen of the elongate body, the fluid can become heated due to its natural resistivity.

Figure 8:
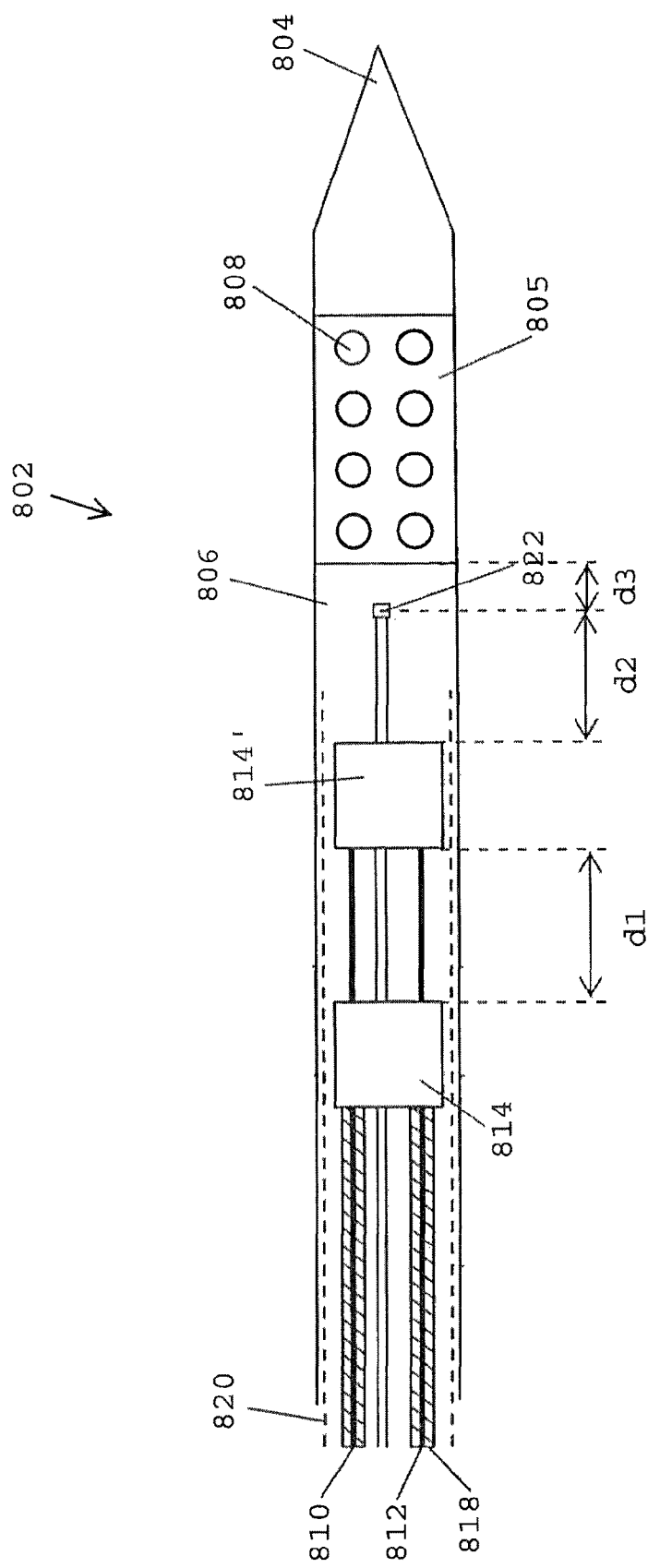
FIG. 8 is a diagram of one embodiment of a heating element in an elongate body of a fluid enhanced ablation device.

FIG. 8 illustrates one embodiment of a heating element including two wires and two spacers. An elongate body 802, similar to elongate body 502, having a proximal end and a pointed distal end 804 includes an inner lumen 806. The elongate body 802 can also include at least one ablation element, such as emitter electrode 805, that is configured to deliver RF energy to tissue surrounding the elongate body 802. The electrode 805 also includes one or more outlet ports 708 configured to deliver fluid from the inner lumen 806 into surrounding tissue.

Disposed within the inner lumen 806 is a heating assembly that includes two wires 810, 812 that are suspended a distance apart by one or more spacers 814, 814'. The wires 810, 812 can be connected to a power source such that electrical energy can be passed between the wires through the fluid flowing in the inner lumen 806. The passage of electrical (e.g., RF) energy through the fluid in the inner lumen 806 can cause the fluid to increase in temperature due to the natural electrical resistivity of the fluid, similar to the mechanism discussed above by which tissue surrounding the elongate body can be heated using RF energy. The wires 810, 812 can be formed from any conductive material, similar to the materials discussed above in connection with the electrode 205. In one embodiment, however, the wires 810, 812 can be formed from silver wire and can have an exposed chlorided surface between or adjacent to the spacers 814, 814'. As discussed above, these materials can participate in an ion exchange process that minimizes the voltage drop across the wire/fluid interface and prevents excessive heating of the surrounding fluid.

In order to effectively pass energy through the fluid flowing within the inner lumen 806, in an exemplary embodiment, the wires 810, 812 (or at least the exposed portion of the wires) are held in an optimum relation to one another by the spacers 814, 814'. This prevents the wires from contacting each other and producing an electrical short. In some embodiments, the wires 810, 812 are exposed for only a short distance located just proximal of the electrode 805 and outlet ports 808. As shown in FIG. 8, the wires can be exposed for a distance $d_1$ between the two spacers 814, 814' that are positioned at a proximal and a distal end of a distal portion of the wires. The distance $d_1$ can vary and, in one embodiment, can be about 5 mm. Proximal to the spacer 814, the wires 810, 812 can be covered in an electrically insulating material 818 to prevent the passage of electrical energy therebetween. In addition, the wires 810, 812 can also be prevented from directly contacting the elongate body 802, as an electrical short can result from both of the wires 810, 812 simultaneously contacting the electrically conductive elongate body. Accordingly, in some embodiments, the elongate body 802 can be lined with an insulating material 820, such as a plastic tube, liner, or coating disposed on the inner walls of the elongate body 802.

The inner lumen 806 can also house one or more temperature sensors to monitor and assist in controlling the heating of fluid flowing within the inner lumen. The embodiment illustrated in FIG. 8 includes a chromel-constantan fine-wire thermocouple configured to float in the fluid distal of the spacer 814' by a distance $d_2$. One skilled in the art will appreciate that thermocouples are just one example of temperature sensors that can be employed to measure the temperature of the flowing fluid and that a variety of sensors, including thermistors and diodes, can also be used. Further, distance $d_2$ can vary and, in one embodiment, it can be about 10 mm. The thermocouple 822 can also be disposed a distance $d_3$ proximal to the electrode 805 and outlet ports 808. While this distance can vary as well, in one embodiment, the distance $d_3$ is about 2 mm. The distances $d_1$, $d_2$, and $d_3$ (and the corresponding positions of the spacers 814, 814') can be chosen to allow for sufficient heating of fluid flowing in the inner lumen 806, as well as to allow sufficient mixing of the heated fluid prior to flowing through outlet ports 808 so as to assure that the fluid being injected into tissue surrounding the elongate body 802 has a uniform temperature. However, the distances $d_2$ and $d_3$ should be minimized such that heating of the fluid flowing within the inner lumen 806 occurs as close to the outlet ports 808 as possible. This configuration minimizes the thermal losses and unintentional environmental heating associated with transporting heated fluids from remote locations within a patient's body.

Figure 9:
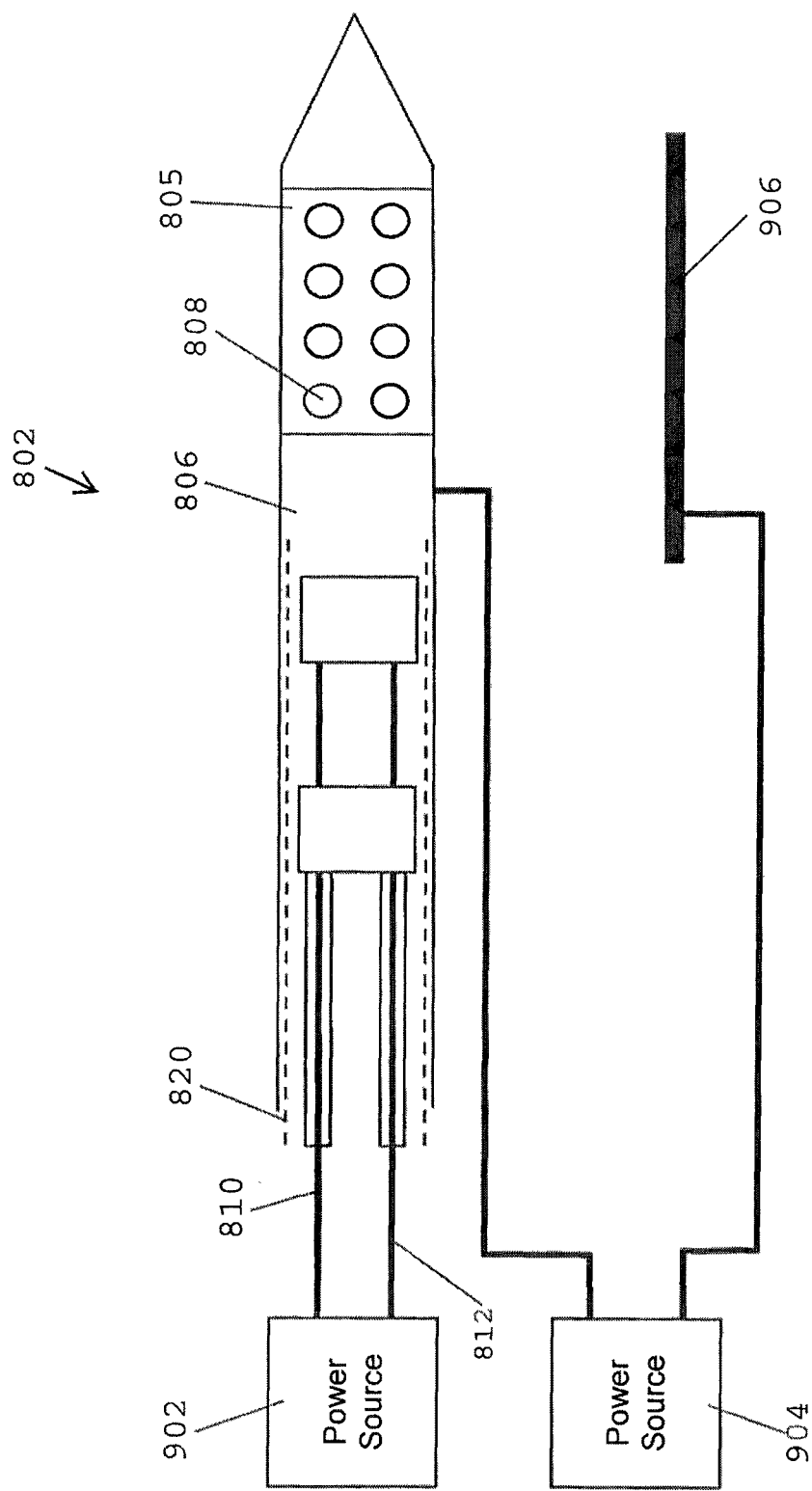
FIG. 9 is a diagram of one embodiment of an electrical circuit for driving a fluid enhanced ablation device.

FIG. 9 illustrates an exemplary electrical circuit for delivering RF energy to both tissue surrounding the elongate body 802 and fluid flowing through the inner lumen 806 of the elongate body 802. In the illustrated embodiment, two separate power sources 902, 904 are utilized to deliver electrical energy including, for example, RF energy. The power source 902 can be connected to the two wires 810, 812 running through the inner lumen 806 of the elongate body 802. By passing electrical current through the wires, energy can be transmitted through the fluid flowing within the inner lumen 806 between the exposed portions of the wires 810, 812.

The power source 904 can be connected to both the elongate body 802 and a collector electrode 906. The collector electrode can be located remotely on a patient's body, for example, placed under a patient's back on an operating table. In other embodiments, the collector electrode 906 can be co-located on the elongate body 802 or it can be located on a second elongate body positioned nearby the elongate body 802.

The power source 904 can deliver RF energy from the electrode 805 to the collector electrode 906 by passing electrical current through the elongate body 802. The two power sources 902, 904 do not share a common electrical ground and therefore remain electrically isolated from one another. This ensures that power from the source 902 heats only saline flowing within the elongate body 802, while power from the source 904 heats only tissue surrounding the elongate body 802. The spacers and insulating materials discussed above prevent a short between the two wires 810, 812 that can result from the wires touching each other or simultaneously contacting the elongate body 802. One skilled in the art will appreciate that a variety of combinations of spacers and insulating materials covering the wires and/or the inner walls of the elongate body can be used to prevent such an electrical short circuit.

In an exemplary embodiment, as saline solution is pumped through the elongate body's inner lumen 706, the saline can be heated above body temperature by the power source 802, preferably to between about 50° C. and about 70° C. This can be accomplished by delivering RF energy to the fluid within the inner lumen 706 via the wires 710, 712. For example, typical fluid enhanced ablation therapy operating parameters involve the application of 20 volts or more to the wires 710, 712. In some embodiments, the applied voltage can go as high as 120 volts and, in some embodiments, can be about 30 volts (e.g., 31.25 volts in one embodiment). The heated, flowing saline solution can be subsequently injected into tissue surrounding the elongate body 702 via the outlet ports 708 at a variety of flow rates. For example, in some embodiments fluid can be ejected from the elongate body 702 at a flow rate of about 10 ml/min. The delivery of heated fluid can be done independently or in conjunction with the delivery of ablative energy from the power source 804. The operating parameters of fluid enhanced ablation therapy can vary according to a number of factors, including the desired therapeutic effect, the geometry and tissue properties of the treatment volume, etc. By way of example, in one embodiment ablation therapy conducted in a patient's liver can heat saline to 50° C. using 40 watts of power and deliver the saline at 10 ml/min for about 5 minutes. By way of further example, ablation therapy using these same parameters can be delivered for only about 90 seconds when treating cardiac tissue. While the particular properties of the intended treatment site will ultimately govern the selected operating parameters, fluid enhanced ablation therapy typically involves the delivery of saline at a rate between about 0 and about 20 ml/min. The saline is typically heated to between about 50° C. and 80° C. using up to 80 watts of power and up to 120 volts. Fluid heated according to these exemplary operating parameters can be combined with electrical energy delivered directly to the tissue to conduct ablation therapy. In some embodiments, up to 100 watts of power can be applied to the tissue from, for example, an emitter electrode.

While the preceding discussion has described a two wire, two spacer heating element configuration, other configurations are possible as well. Further information on heating elements for use in fluid enhanced ablation therapy is available in U.S. Pat. No. 6,328,735 to Curley et al. and U.S. patent application Ser. No. 13/445,036, filed on Apr. 12, 2012, and entitled "Methods and Devices for Heating Fluid in Fluid Enhanced Ablation Therapy." The contents of each of these references are hereby incorporated by reference in their entirety.

Figure 10:
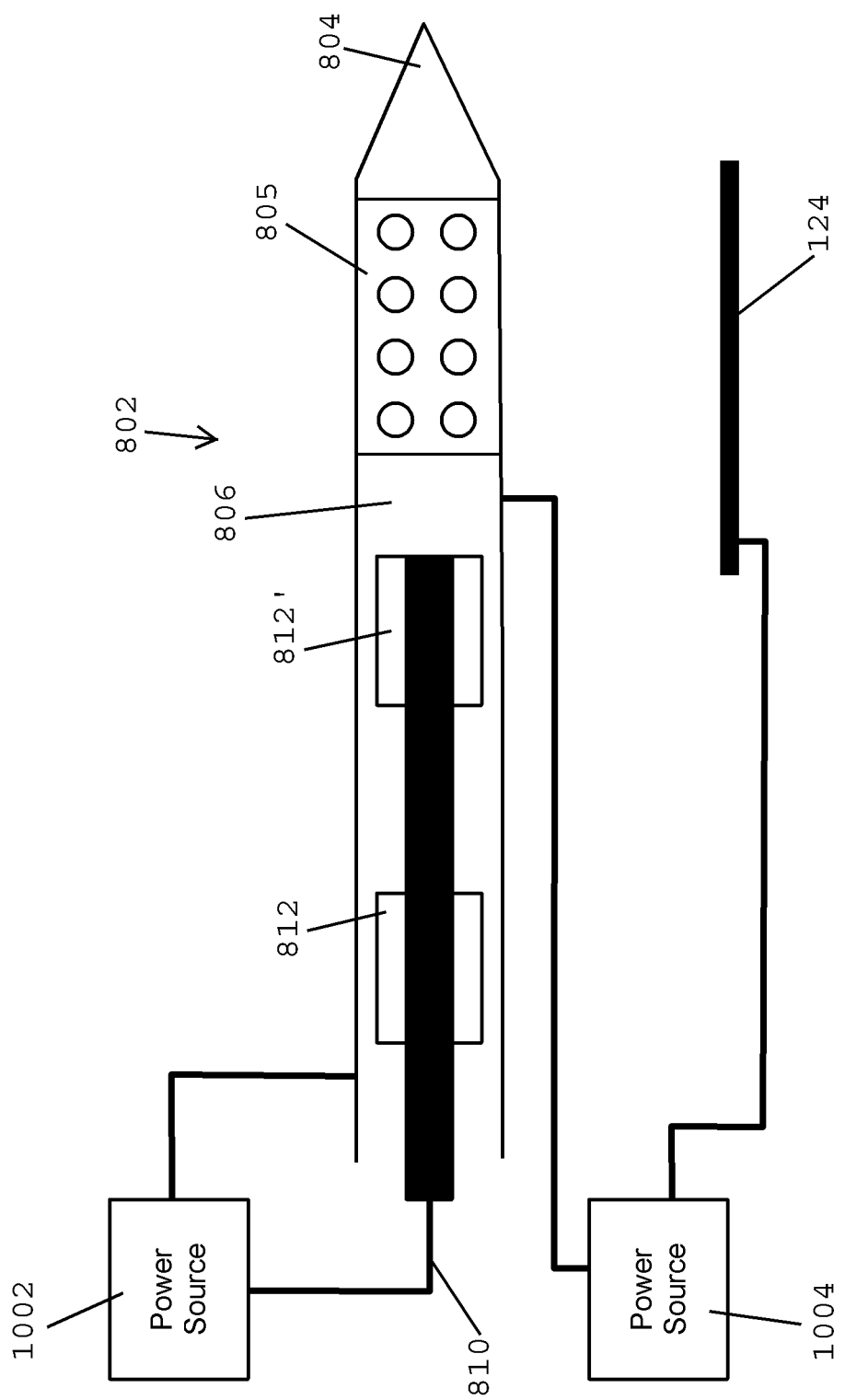
FIG. 10 is a diagram of one embodiment of an electrical circuit for driving an elongate body having a single-wire heating assembly.

For example, FIG. 10 illustrates one embodiment of an electrical circuit for independently delivering RF energy to fluid flowing in the inner lumen 806 of the elongate body 802, as well as to tissue surrounding the elongate body when using a heating assembly with a single wire and a conductive elongate body or a conductive tube placed within the elongate body. As shown in the figure, dual power sources 1002, 1004 are used to deliver energy to the fluid within the inner lumen 806 and the tissue surrounding the elongate body 802, similar to the circuit illustrated in FIG. 9. However, in the illustrated embodiment, the circuits formed by each power source 1002, 1004 share the elongate body 802 as a common electrode. In other words, power source 1002, which is configured to deliver RF energy to fluid flowing within the inner lumen 806, is connected to the wire 810 disposed within the inner lumen 806 and to the elongate body 802 itself. The elongate body 802, then, serves as an electrode for the power source 1002. The power source 1004, on the other hand, is connected to the elongate body 802 and the collector electrode 124. Accordingly, the power source 1004 can deliver RF energy from the electrode 805 into tissue surrounding the elongate body 802. As a result of the fact that the two power sources 1002, 1004 are only connected via the elongate body 802 (i.e., only connected at a single point without a return connection), the power sources are able to operate independently and simultaneously without any current flowing therebetween.

Methods for the administration of fluid enhanced ablation therapy using the low profile devices described herein are also provided. For example, a method for administering fluid enhanced ablation therapy can include percutaneously inserting a distal end of an elongate body of an ablation device into a patient's body. The method can further include manipulating the distal end of the elongate body within the patient's body using a low profile handle coupled to the proximal end of the elongate body and having a longitudinal axis that extends at an angle to a longitudinal axis of the elongate body. Finally, the method can include delivering fluid through the elongate body of the ablation device into tissue surrounding the distal end of the elongate body while simultaneously delivering energy into tissue surrounding the distal end of the elongate body.

Manipulating and delivering fluid and energy through a low profile device having a handle extending at an angle to the longitudinal axis of the elongate body can reduce the amount of clearance required around a patient due to the decreased overall length of the ablation therapy device. Furthermore, the decreased clearance space can allow fluid enhanced ablation therapy procedures to be carried out in conjunction with medical imaging without having to repeatedly remove and reintroduce the ablation devices being used.

For example, in some embodiments, methods for administering fluid enhanced ablation therapy can include imaging at least a portion of the patient using a medical imaging apparatus. When the low profile devices and methods of the invention are utilized, imaging can occur simultaneously with any of the method steps for manipulating the devices or delivering fluid and energy into tissue surrounding the elongate bodies inserted into tissue. Still further, in some embodiments, both the method steps for manipulating the devices and delivering fluid and energy into tissue can be conducted inside a medical imaging apparatus, such as the CT scanner 400. Other exemplary medical imaging apparatuses include, for example, an MRI scanner, an ultrasound scanner, and an X-ray scanner.

In other embodiments, the methods of the invention can also include heating the fluid inside the elongate body prior to delivering the fluid into the tissue surrounding the elongate body. This can be accomplished, for example, by passing energy through one or more wires disposed within the inner lumen of the elongate body, as discussed above.

The low profile devices disclosed herein can be designed to be disposed after a single use, or they can be designed for multiple uses. In either case, however, the devices can be reconditioned for reuse after at least one use. Reconditioning can include any combination of the steps of disassembly of a device, followed by cleaning or replacement of particular pieces, and subsequent reassembly. In particular, a device can be disassembled, and any number of the particular pieces or parts of the device can be selectively replaced or removed in any combination. Upon cleaning and/or replacement of particular parts, a device can be reassembled for subsequent use either at a reconditioning facility or by a surgical team immediately prior to a surgical procedure. Those skilled in the art will appreciate that the reconditioning of a device can utilize a variety of techniques for disassembly, cleaning/replacement, and reassembly. Use of such techniques, and the resulting reconditioned device, are all within the scope of the present invention.

For example, the devices disclosed herein may be disassembled partially or completely. In particular, the elongate body portion of any device can be removed from the handle portion of the device, or the elongate body and handle can be decoupled from the electrical and fluid connections joining the device to the remainder of the fluid enhanced ablation system. In other embodiments, solely the distal portion of an elongate body (e.g., on the portion that extends into a patient's body) can decouple from a proximal portion that can remain connected to the handle of the device. In yet another embodiment, the handle, elongate body, and connections can be removably coupled to a housing that contains, for example, the fluid reservoir, pump, and power supply and controller shown in FIG. 2. These are exemplary disassembly steps only, as any component of the device can be configured to separate from the device for cleaning and/or replacement.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility.

In many embodiments, it is preferred that the device is sterilized. This can be done by any number of ways known to those skilled in the art including beta or gamma radiation, ethylene oxide, steam, and a liquid bath (e.g., cold soak). In certain embodiments, the materials selected for use in forming components such as the elongate body may not be able to withstand certain forms of sterilization, such as gamma radiation. In such a case, suitable alternative forms of sterilization can be used, such as ethylene oxide.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:
1. An ablation device, comprising:
   a conductive elongate body having
      proximal and distal ends,
      an inner lumen extending longitudinally through the elongate body, and
      at least one outlet port formed in the elongate body configured to deliver fluid to tissue surrounding the elongate body;
   at least one heating element disposed within the inner lumen of the elongate body and configured to heat fluid passing therethrough, the at least one heating element including a single wire that extends through at least one spacer, where the single wire is configured to pass electrical energy through the fluid flowing through the inner lumen of the elongate body and the at least one spacer is configured to maintain a position of the single wire within the inner lumen of the elongate body;
   a first power source configured to heat fluid flowing through the inner lumen by passing current between the single wire and the elongate body;
   a second power source configured to heat tissue surrounding the elongate body by passing current between the elongate body and a collector electrode positioned outside the inner lumen and
   a handle having proximal and distal ends, the distal end of the handle being coupled to the proximal end of the elongate body;
   wherein a longitudinal axis of the elongate body extends at an angle to a longitudinal axis of the handle and wherein the handle is contoured along a longitudinal length thereof such that the handle forms a concave curve facing the distal end of the elongate body.

2. The ablation device of claim 1, wherein the angle between the longitudinal axis of the elongate body and the longitudinal axis of the handle is in a range of about 10 degrees to about 120 degrees.

3. The ablation device of claim 1, wherein the angle between the longitudinal axis of the elongate body and the longitudinal axis of the handle is in a range of about 30 degrees to about 100 degrees.

4. The ablation device of claim 1, wherein the angle between the longitudinal axis of the elongate body and the longitudinal axis of the handle is in a range of about 45 degrees to about 90 degrees.

5. The ablation device of claim 1, wherein the angle between the longitudinal axis of the elongate body and the longitudinal axis of the handle is about 90 degrees.

6. The ablation device of claim 1, wherein the handle includes an inner lumen extending therethrough.

7. The ablation device of claim 6, wherein the inner lumen extending through the elongate body is in communication with the inner lumen extending through the handle.

8. The ablation device of claim 1, further comprising an insertion stopping element slidably disposed on the elongate body.

9. The ablation device of claim 1, wherein the handle is formed from a non-magnetic material.

10. The ablation device of claim 1, wherein the handle includes a surface texture to improve a user's grip of the handle.

11. The ablation device of claim 1, wherein the single wire is covered in an electrically insulating material and is exposed for only a short distance located just proximal of the at least one outlet port.

12. The ablation device of claim 1, wherein the inner lumen of the elongate body is lined with an insulating material.

13. An ablation device, comprising:
   an elongate body having
      proximal and distal ends,
      an inner lumen extending longitudinally through the elongate body, and at least one outlet port formed in the elongate body configured to deliver fluid to tissue surrounding the elongate body;

at least one ablation element disposed along a length of the elongate body adjacent to the at least one outlet port and configured to deliver energy to tissue surrounding the elongate body;

at least one heating element disposed within the inner lumen of the elongate body and configured to heat fluid passing therethrough, the at least one heating element including two wires that extend through two spacers, where the two wires are configured to pass electrical energy through the fluid flowing through the inner lumen of the elongate body from an exposed portion extending between the two spacers and the two spacers are configured to maintain a position of the two wires within the inner lumen of the elongate body; and a handle having proximal and distal ends, the distal end of the handle being coupled to the proximal end of the elongate body;

wherein a longitudinal axis of the elongate body extends at an angle to a longitudinal axis of the handle and wherein the handle is contoured along a longitudinal length thereof such that the handle forms a concave curve facing the distal end of the elongate body.

14. An ablation device, comprising:

an elongate body having
proximal and distal ends,
an inner lumen extending longitudinally through the elongate body, and
at least one outlet port formed in the elongate body configured to deliver fluid to tissue surrounding the elongate body;

at least one ablation element disposed along a length of the elongate body adjacent to the at least one outlet port and configured to deliver energy to tissue surrounding the elongate body;

at least one heating element disposed within the inner lumen of the elongate body and configured to heat fluid passing therethrough, the at least one heating element including at least one wire covered in an electrically insulating material and exposed for only a short distance located just proximal of the at least one outlet port that extends through at least one spacer, where the at least one wire is configured to pass electrical energy through the fluid flowing through the inner lumen of the elongate body and the at least one spacer is configured to maintain a position of the at least one wire within the inner lumen of the elongate body; and a handle having proximal and distal ends, the distal end of the handle being coupled to the proximal end of the elongate body;

wherein a longitudinal axis of the elongate body extends at an angle to a longitudinal axis of the handle and wherein the handle is contoured along a longitudinal length thereof such that the handle forms a concave curve facing the distal end of the elongate body.

15. An ablation device, comprising:

an elongate body having
proximal and distal ends,
an inner lumen extending longitudinally through the elongate body that is lined with an insulating material, and
at least one outlet port formed in the elongate body configured to deliver fluid to tissue surrounding the elongate body;

at least one ablation element disposed along a length of the elongate body adjacent to the at least one outlet port and configured to deliver energy to tissue surrounding the elongate body;

at least one heating element disposed within the inner lumen of the elongate body and configured to heat fluid passing therethrough, the at least one heating element including at least one wire that extends through at least one spacer, where the at least one wire is configured to pass electrical energy through the fluid flowing through the inner lumen of the elongate body and the at least one spacer has a length that is less than a length of the elongate body and is configured to maintain a position of the at least one wire within the inner lumen of the elongate body; and a handle having proximal and distal ends, the distal end of the handle being coupled to the proximal end of the elongate body;

wherein a longitudinal axis of the elongate body extends at an angle to a longitudinal axis of the handle and wherein the handle is contoured along a longitudinal length thereof such that the handle forms a concave curve facing the distal end of the elongate body.

16. The ablation device of claim 1, wherein the elongate body is configured for insertion into tissue.

17. The ablation device of claim 16, wherein the elongate body includes a pointed distal tip configured to puncture tissue.

18. The ablation device of claim 13, wherein the elongate body is configured for insertion into tissue.

19. The ablation device of claim 18, wherein the elongate body includes a pointed distal tip configured to puncture tissue.

20. The ablation device of claim 14, wherein the elongate body is configured for insertion into tissue.

21. The ablation device of claim 20, wherein the elongate body includes a pointed distal tip configured to puncture tissue.

22. The ablation device of claim 15, wherein the elongate body is configured for insertion into tissue.

23. The ablation device of claim 22, wherein the elongate body includes a pointed distal tip configured to puncture tissue.

24. The ablation device of claim 1, wherein the at least one spacer has a length that is less than a length of the elongate body.

25. The ablation device of claim 13, wherein the two wires are covered in an electrically insulating material and are exposed for only a short distance located just proximal of the at least one outlet port.

26. The ablation device of claim 13, wherein the elongate body is lined with an insulating material.

27. The ablation device of claim 13, wherein each spacer has a length that is less than a length of the elongate body.

28. The ablation device of claim 14, wherein the at least one spacer has a length that is less than a length of the elongate body.

29. The ablation device of claim 15, wherein the at least one wire is covered in an electrically insulating material and is exposed for only a short distance located just proximal of the at least one outlet port.

30. The ablation device of claim 15, wherein the elongate body is lined with an insulating material.

* * * * *